United States Patent
Adsul et al.

(10) Patent No.: US 11,149,261 B2
(45) Date of Patent: Oct. 19, 2021

(54) **PROVIDENT METHOD OF CELLULASES ENZYMES PRODUCTION BY *PENICILLIUM FUNICULOSUM* MRJ-16 USING LOW COST MEDIA COMPONENTS**

(71) Applicants: INDIAN OIL CORPORATION LIMITED, Mumbai (IN); DEPARTMENT OF BIOTECHNOLOGY, New Delhi (IN)

(72) Inventors: Mukund Adsul, Faridabad (IN); Simranjeet Kaur Sandhu, Faridabad (IN); Reeta Rani Singhania, Faridabad (IN); Anshu Shankar Mathur, Faridabad (IN); Ravi Prakash Gupta, Faridabad (IN); Deepak Kumar Tuli, Faridabad (IN); Suresh Kumar Puri, Faridabad (IN); Sankara Sri Venkata Ramakumar, Faridabad (IN)

(73) Assignees: INDIAN OIL CORPORATION LIMITED, Mumbai (IN); DEPARTMENT OF BIOTECHNOLOGY, New Delhi (IN)

( * ) Notice: Subject to any disclaimer, the term of this patent is extended or adjusted under 35 U.S.C. 154(b) by 69 days.

(21) Appl. No.: 16/698,666

(22) Filed: Nov. 27, 2019

(65) Prior Publication Data

US 2020/0165589 A1    May 28, 2020

(30) Foreign Application Priority Data

Nov. 28, 2018 (IN) .............................. 201821044919

(51) Int. Cl.
| | | |
|---|---|---|
| *C12N 9/42* | (2006.01) | |
| *C12N 1/14* | (2006.01) | |
| *C12P 21/00* | (2006.01) | |
| *C12R 1/80* | (2006.01) | |

(52) U.S. Cl.
CPC .............. *C12N 9/2437* (2013.01); *C12N 1/14* (2013.01); *C12N 1/145* (2021.05); *C12P 21/00* (2013.01); *C12P 2203/00* (2013.01); *C12R 2001/80* (2021.05)

(58) Field of Classification Search
CPC .......... C12N 9/2437; C12N 1/14; C12R 1/80; C12P 21/00; C12P 2203/00
See application file for complete search history.

(56) References Cited

U.S. PATENT DOCUMENTS

| | | | | |
|---|---|---|---|---|
| 4,931,352 | A * | 6/1990 | Fromtling | ................. C07K 7/56 435/71.3 |
| 8,043,844 | B2 | 10/2011 | Sabatier et al. | |
| 8,956,846 | B2 | 2/2015 | Ben Chaabane et al. | |
| 2014/0363846 | A1 | 12/2014 | Edwards et al. | |
| 2020/0102621 | A1* | 4/2020 | Adsul | ...................... C12N 1/22 |

FOREIGN PATENT DOCUMENTS

| | | |
|---|---|---|
| CN | 103045484 B | 12/2014 |
| RU | 2261910 C2 | 10/2005 |

OTHER PUBLICATIONS

Ogunmolu et al. Comparative insights into the saccharification potentials of a relatively unexplored but robust Penicillium funiculosum glycoside hydrolase 7 cellobiohydrolase. Biotechnol Biofuels (Mar. 20, 2017), 10(71). (Year: 2017).*
Ghose, T.K. "Measurement of cellulase activities" Pure and Applied Chemistry, vol. 59, No. 2, pp. 257-268 (1987).
Smith, PK et al., "Measurement of protein using bicinchoninic acid" Analytical Biochemistry, vol. 150, No. 1, pp. 76-85 (1985).
Ahmed, S. et al., "Production and Purification of Cellulosedegrading Enzymes From a Filamentous Fungus Trichoderma Harzianum," Pakistan Journal of Botany, vol. 41, No. 3, pp. 1411-1419 (Jun. 2009).
Bansal, N. et al., "Production of cellulases from Aspergillus niger NS-2 in solid state fermentation on agricultural and kitchen waste residues," Waste Management, vol. 32, Issue 7, pp. 1341-1346 (Apr. 12, 2012).
Brijwani, K. and Vadlani, P. V., "Cellulolytic Enzymes Production via Solid-State Fermentation: Effect of Pretreatment Methods on Physicochemical Characteristics of Substrate," Enzyme Research, vol. 2011, Article ID 860134, 10 pages (Jun. 2011).
Fawzi, E. M. "Production and Purification of β-Glucosidase and Protease by Fusarium proliferatum NRRL 26517 Grown on Ficus nitida Wastes," Annals of Microbiology, vol. 53, Issue 4, pp. 463-476 (2003).

* cited by examiner

*Primary Examiner* — Sean C. Barron
(74) *Attorney, Agent, or Firm* — Maschoff Brennan

(57) ABSTRACT

The present invention relates to a method of cellulases enzymes production by *Penicillium funiculosum* MRJ-16 using minimum media components and/or low cost media components like cellulose or pretreated lignocellulosic biomass as carbon source and soya flour or defatted soya flour or de-oiled soya cake as nitrogen source. The present invention also provides a method for production of high titer of cellulases and hemicellulases enzymes using *Penicillium funiculosum* MRJ-16 using minimum media and/or low cost media components.

8 Claims, No Drawings

PROVIDENT METHOD OF CELLULASES ENZYMES PRODUCTION BY *PENICILLIUM FUNICULOSUM* MRJ-16 USING LOW COST MEDIA COMPONENTS

FIELD OF THE INVENTION

The present invention provides for a method of cellulases enzymes production by *Penicillium funiculosum* MRJ-16 using minimum media components. The present invention also provides a method for production of high titer of cellulases and hemicellulases enzymes using *Penicillium funiculosum* MRJ-16 using minimum media components.

BACKGROUND OF THE INVENTION

Fossil fuels depletion and its usage have inevitably led to an unfavorable impact on our environment and has subsequently lead to focus on development of sustainable technology to produce bio-fuels. To produce bio-fuels, lignocellulosic biomass which is cheaper, renewable and easily available in surplus quantity is preferred. The structure of lignocellulosic biomass consists of three major polymers: cellulose, hemicellulose and lignin along with small amount of phenolic substitutes, minerals and acetyl groups etc. Cellulose and hemicellulose polymer in lignocellulosic biomass is degraded to produce pentoses and hexoses sugars, which can be utilized for the production of ethanol after alcoholic fermentation. Degradation requires separation of cellulose and hemicelluloses from lignocellulosic biomass by chemical and physical pretreatment followed by enzymatic hydrolysis. Enzymatic hydrolysis of lignocellulosic biomass requires synergistically acting variety of cellulolytic, hemicellulolytic, lignin degrading, auxiliary and non-catalytic proteins.

Advancement in enzyme production process is required to transform cellulosic biomass to ethanol in an economical way, as it accounts for 30% of overall process cost. The major challenge in enzyme production process is production of enzymes at high titer, high specificity and well-balanced enzyme mixture using cheaper substrates. In Industry, different species of genus *Trichoderma, Penicillium, Aspergillus* and *Humicola* fungi have attracted interest as cellulases and hemicellulases enzyme producers. Different genetic modifications have been done by conventional and recombinant techniques in these fungal strains to produce desired titer of enzymes. Mutant created after genetic manipulation by recombinant DNA technology required specific growth factors or media components to produce enzymes.

The method of cultivating micro-organisms and production of cellulase enzymes requires a complex regulation mechanism in a reactor. The efficiency of a fungus in terms of cellulase production depends upon the medium, cultural parameters and operational conditions like temperature, pH, agitation rate and dissolved oxygen etc. Hence, the formulation of suitable fermentation strategies plays a major role in deciding the fate of the fungus. The aforementioned strategies include cheap carbon source for fungal growth and an inducer to trigger the production of specific enzymes that need to be added at a specific rate because too high a rate of supply leads to a process shift towards fungal biomass accumulation, while too low a supply rate leads to deterioration of fungal biomass. Adequate dissolved oxygen is required to maintain the cell growth and metabolism during fermentation process. Similarly, previous studies have shown that the optimal pH for fungal cellulases varies from species to species. According to Bansal et al. (2012) the optimum pH which supported maximum production of cellulases by *A. niger* NS-2 was pH 7. However, Fawzi (2003) reported pH 5.0 to be optimum for production of β-glucosidase by *Fusarium proliferatum* NRRL26517 strain. Thus, it is important to understand the pH optima for maximum cellulase production from fungi strain used.

Thus, the present invention concerns with the development of a process of production of cellulases enzymes mixture at high titer from fungal mutant strain in an economical way by using cheaper media components and its usage thereof.

U.S. Pat. No. 8,956,846 B2 discloses the production of cellulases enzymes using *Trichoderma reesei* CL847 strain in continuous fermentation process. In this method glucose at 15 g/l concentration was used for the growth of fungus followed by continuous supply of lactose (250 g/l) as inducer at 4 ml/hour rate to support enzyme production process. The supply of inducer was regulated through regulation of the dissolved oxygen partial pressure in the medium. Inducer was supplied when the oxygen partial pressure was greater than 50% of the saturation oxygen pressure and it was stopped when the oxygen partial pressure was less than 40%. The final protein was 43.6 g/L, specific activity of filter paper unit (FPU) and β-glucosidase was 0.78 and 1.60 International Unit (IU)/mg respectively. FPU and β-glucosidase enzymes were present in 1:2 ratios respectively which is insufficient for the lignocellulosic substrate hydrolysis. Thus, additional β-glucosidase is required. However, use of glucose and lactose as carbon sources will not only escalate the production cost but also poses challenging question for long term supply of these commodities along with raising the commodity prices.

US 2014/0363846 discloses cultured fungi belonging to genus *Myceliophthora* by submerged fermentation to produces cellulases enzyme. Carbon sources used were soluble non cellulase-inducing carbon sources such as glycerol, xylose, glucose, glucose: xylose (90:10), sucrose, glucose and inducing substrate like sophorose, molasses, gentibiose, cellobiose, fructose and glucose: fructose (50:50). When glucose alone and with any of the inducing substrate mentioned above was used as carbon sources, similar results were observed but maximum activity of 0.55 FPU/mg proteins was detected when only xylose was used as carbon source. This patent application mentioned about the presence of variety of cellulases, hemicellulases, lignin degrading enzymes, estrases, swollenin and expansins secreted by the *Myceliophthora thermophila* strain (ATCC No. 42464) used but no activity of above mentioned expect Filter paper activity were presented.

CN103045484B (2014) discloses *Penicillium decumbens* (CCTCC M2011195) mutant strain created by using UV irradiation and a chemical mutagen NTG (N-methyl-N'-nitro-Nnitrosoguanidine). This mutant strain was used for cellulases production using the fermentation media composed of fishing xylose, ammonium sulfate, wheat bran, potassium phosphate monobasic, microcrystalline cellulose, and magnesium salt. Filter paper activity of 10 IU/ml, endoglucanase activity of 30 IU/ml, exo-glucanase activity of 1.5 IU/ml and β-glucosidase of 8 IU/ml was observed. The β-glucosidase activity obtained was low and the choice of carbon source as fishing xylose and nitrogen source as wheat bran can leads to enzyme production process uneconomical and non-sustainable.

Ahmed et al relates to a minireview on production and application of fungal cellulases. The review briefly discusses the production of fungal cellulases focusing on the parameters affecting their production based on relevant publications. The review highlights the efficient and cost-effective production of cellulases from *Penicillium* sp. indicating fundamental roles of the fermentation media, pH, incubation time, temperature and aerations on the level of cellulose production. NPL1 further discloses that suitable fermentation media for cellulase production comprises rice straw as the carbon source and soyaben meal as the nitrogen source. Additionally, Ahmed et al. discloses that optimal cellulose production is achieved at pH 5.0 and temperature 30° C.

Brijwani et al relates to a cost-effective method of production of a cellulolytic enzyme system in mixed-culture solid-state fermentation of soybean hulls supplemented with wheat bran. NPL2 discloses that parameters like pH and temperature are required to be optimized to achieve improved enzyme activity. Thus, optimum temperature of 30° C. and pH of 5 were maintained during the process of fermentation. Brijwani et al refers to the use of *Penicillium* fungal strain for the production of cellulase enzyme but does not focus on a particular strain. Further, Brijwani et al discloses the use of soybean hull and wheat bran as substrate for fermentation and indicates that appreciable enzyme levels were achieved upto an incubation time of 96 hours.

RU 2261910 C2 relates to a strain of *Penicillium funiculosum* that is employed for efficient production of enzyme complex including cellulases. RU 2261910 C2 discloses that the microorganism used for the preparation of enzymes of the present invention are grown under aerobic conditions in a medium which contains cellulose, corn steep syrup, calcium carbonate and ammonium sulfate. Further, RU 2261910 C2 also indicates that optimum levels of enzyme production is achieved at pH ranging from 3.0-6.0 and at a temperature between 27° C. and 36° C.

SUMMARY OF THE INVENTION

An object of the present invention is to produce high titer of cellulases and hemicellulases enzymes using minimum media components and/or low cost media components like cellulose or pretreated lignocellulosic biomass as carbon source and soya flour or defatted soya flour or de-oiled soya cake as nitrogen source along with hyper-cellulolytic *Penicillium funiculosum* MRJ-16.

The present invention provides a process for producing cellulases and hemicellulases enzymes, employing *Penicillium funiculosum* MRJ-16, with Accession No. MTCC-25142, and date of deposition as 12 Jun. 2017, deposited at the Institute of Microbial Technology £IMTECH), Sector 39A, Chandigarh-160036. *P. funiculosum* MRJ-16 MTCC 25142 is a mutant strain of *P. funiculosum* NCIM 1228. This mutant is isolated through a combined mutagenesis and isolation method wherein diethyl sulfate and UV were used and selected is made on glucose and cellulose-containing solid media. This mutant produces higher cellulase than parent strain i.e., NCIM 1228. *P. funiculosum* MRJ-16 MTCC 25142 mutant shows catabolite repressed characteristic and produces enzyme even in glucose containing media. The changes in the genome and characteristics were mentioned in the patent US20200102621A1. This is characterized by the ability to produce high titer of enzyme mixture comprising FPase, CMCase, Cellobiase, β-glucosidase, endoglucanase, α-L arabinofuranosidase, β-xylosidase, xylanase, pectinase, cellobiohydrase and oxidases and produce enzymes in the presence of a catabolite repressor molecule like glucose and/or xylose. The titer of enzyme mixture produced using mutant fungal strain MRJ-16 is at least two-fold higher than naive *Penicillium funiculosum* strain NCIM 1228, when used in a fermentation process. The mutant strain 'MRJ-16' is with high hydrolytic activity and catabolite derepressed character.

The present invention provides a process for cellulases enzyme production employing *Penicillium funiculosum* MRJ-16 mutant, the process comprising conducting fermentation in a fermentation media comprising:
(a) about 1-5% w/v of cellulose, acid pretreated lignocellulosic biomass or a combination thereof; and
(b) about 1-5% w/v soya flour or defatted soya flour or de-oiled soya cake.

The present invention provides a process for cellulases enzyme production employing *Penicillium funiculosum* MRJ-16 mutant, the process comprising conducting fermentation in a fermentation media comprising:
(a) about 1-5% w/v carbon source selected from cellulose, acid pretreated lignocellulosic biomass or a combination thereof;
(b) about 1-5% w/v soya flour or defatted soya flour or de-oiled soya cake as nitrogen source.

In a preferred feature, the process for cellulases enzyme production according to the present invention comprises:
(a) providing a fermentation media containing a carbon source and a nitrogen source;
(b) maintaining the temperature of fermentation media in the range of 25 to 34° C.;
(c) adjusting the pH of the fermentation media to about 5 to 5.5;
(d) providing aeration of about 50%;
(e) inoculating the fermentation media with about 10% active liquid seed of *Penicillium funiculosum* MRJ-16 and fermenting;
(f) allowing the fermentation process for about 96 hours,
(g) collecting the enzyme broth and centrifuging to obtain enzymes.

In a preferred feature, in the process for cellulases enzyme production of the present invention, the fermentation media comprises about 1-5% w/v carbon source selected from cellulose, acid pretreated lignocellulosic biomass or a combination thereof; and about 1-5% w/v soya flour or defatted soya flour or de-oiled soya cake as nitrogen source.

In a preferred feature, the carbon source in the fermentation media is cellulose and acid pretreated lignocellulosic biomass in ratios selected from 1:1 or 1:2.

In another preferred feature, in the process for cellulases enzyme production of the present invention, the pH during the fermentation process is not regulated. In another preferred feature, the aeration during the fermentation process is maintained above 30%. In another preferred feature, prior to fermentation, the fermentation media is sterilized by autoclaving at about 120° C. for about 20 minutes.

In a further preferred feature, the lignocellulosic biomass for the fermentation is selected from rice straw, wheat straw, corn stover, cotton stalk or sugarcane bagasse. In a preferred feature, the acid pre-treatment of lignocellulosic biomass is done by conc. Sulphuric acid. In another preferred feature, the soya flour for the fermentation media is selected from defatted soya flour or plain soya flour.

In yet another preferred feature, the present invention provides a process for producing cellulases and hemicellulases enzymes, the process comprising the steps of:
(a) preparing media components of fermentation media using 1-5% w/v carbon source selected from cellulose or acid pretreated lignocellulosic biomass and 1-5% w/v soya flour or defatted soya flour or de-oiled soya cake as nitrogen source;

(b) inoculating the media components of step (a) with 10% active liquid seed of *Penicillium funiculosum* MRJ-16;

(c) subjecting the *Penicillium funiculosum* MRJ-16 culture of step (b) to fermentation in an aerated fermenter;

(d) collecting the enzyme broth after the fermentation process of step (c) and subjecting the broth to centrifugation to obtain the enzymes.

The present invention further provides a process for producing cellulases and hemicellulases enzymes, wherein the fermentation of step (c) is carried out at a temperature of about 25 to 34° C.

The present invention further provides a process for producing cellulases and hemicellulases enzymes, wherein the fermentation of step (c) is carried out at a temperature of about 30° C.

The present invention further provides a process for producing cellulases and hemicellulases enzymes, wherein the fermentation of step (c) is carried out for about 96 hours.

The present invention further provides a process for producing cellulases and hemicellulases enzymes, wherein the aeration in the aerated fermenter is maintained above 30%.

The present invention further provides a process for producing cellulases and hemicellulases enzymes, wherein the fermentation of step (c) is carried out at a pH of about 5 to 5.5.

The present invention further provides a process for producing cellulases and hemicellulases enzymes, wherein the fermentation of step (c) is carried out at a pH of about 5.

DETAILED DESCRIPTION OF THE INVENTION

While the invention is susceptible to various modifications and/or alternative processes and/or solvent system, specific embodiment thereof has been shown by way of examples and will be described in detail below. It should be understood, however that it is not intended to limit the invention to the particular processes and/or temperature, pH, ratios, quantity and strains disclosed, but on the contrary, the invention is to cover all modifications, equivalents, and alternative falling within the spirit and the scope of the invention as defined by the appended claims.

The following description is of exemplary embodiments only and is not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention.

Any particulars and all details set forth herein are used in the context of some embodiments and therefore should not be necessarily taken as limiting factors to the attached claims. The attached claims and their legal equivalents can be realized in the context of embodiments other than the ones used as illustrative examples in the description below.

For convenience, before further description of the present disclosure, certain terms employed in the specification, and examples are collected here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles "a", "an" and "the" are used to refer to one or to more than one (i.e., to at least one) of the grammatical object of the article.

The terms "comprise" and "comprising" are used in the inclusive, open sense, meaning that additional elements may be included. It is not intended to be construed as "consists of only".

Throughout this specification, unless the context requires otherwise the word "comprise", and variations such as "comprises" and "comprising", will be understood to imply the inclusion of a stated element or step or group of element or steps but not the exclusion of any other element or step or group of element or steps.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the disclosure, the preferred methods, and materials are now described. All publications mentioned herein are incorporated herein by reference.

In comparison to the prior art, present invention is aimed at providing a method to produce cellulases enzymes in batch process using low cost media components in specific quantities along with *Penicillium funiculosum* mutant strain, which in turn increases the commercial viability of the process.

The present invention provides a method of cellulases enzymes production by *Penicillium funiculosum* MRJ-16 (MTCC Accession No. 25142 and date of deposition 12 Jun. 2017) using low cost media components. The present invention also provides a method for production of high titer of cellulases and hemicellulases enzymes using *Penicillium funiculosum* MRJ-16 using low cost media components or minimum media components.

The present invention provides a process for cellulases enzyme production employing *Penicillium funiculosum* MRJ-16 mutant, the process comprising conducting fermentation in a fermentation media comprising:

(a) about 1-5% w/v carbon source selected from cellulose, acid pretreated lignocellulosic biomass or a combination thereof;

(b) about 1-5% w/v soya flour or defatted soya flour or de-oiled soya cake as nitrogen source.

The present invention provides a process for cellulases enzyme production employing *Penicillium funiculosum* MRJ-16 mutant, the process comprising conducting fermentation in a fermentation media consisting essentially of:

(a) about 1-5% w/v carbon source selected from cellulose, acid pretreated lignocellulosic biomass or a combination thereof;

(b) about 1-5% w/v soya flour or defatted soya flour or de-oiled soya cake as nitrogen source; and (c) water.

The present invention provides a process for cellulases enzyme production employing *Penicillium funiculosum* MRJ-16 mutant, the process comprising conducting fermentation in a fermentation media consisting of:

(a) about 1-5% w/v carbon source selected from cellulose, acid pretreated lignocellulosic biomass or a combination thereof;

(b) about 1-5% w/v soya flour or defatted soya flour or de-oiled soya cake as nitrogen source;

(c) a pH adjusting agent; and (d) water.

In a preferred feature, the pH adjusting agent is selected from $CaCO_3$, $NH_4OH$, NaOH, to adjust the pH of the fermentation media to about 5 to 5.5.

In accordance with the present invention, a method for the production of high titer of cellulases and/or hemicellulases enzymes is provided. The method comprises conducting fermentation employing *Penicillium funiculosum* MRJ-16 mutant in a water comprising:
(a) about 1-5% w/v carbon source selected from cellulose, acid pretreated lignocellulosic biomass or a combination thereof;
(b) about 1-5% w/v soya flour or defatted soya flour or de-oiled soya cake as nitrogen source; and
(c) about 2.5-5% $CaCO_3$.

The present invention also provides a process for cellulases enzyme production comprising:
(a) providing a fermentation media containing a carbon source and a nitrogen source;
(b) maintaining the temperature of fermentation media in the range of 25 to 34° C.;
(c) adjusting the pH of the fermentation media to about 5 to 5.5;
(d) providing aeration of about 50%;
(e) inoculating the fermentation media with about 10% active liquid seed of *Penicillium funiculosum* MRJ-16 and fermenting;
(f) allowing the fermentation process for about 96 hours;
(g) collecting the enzyme broth and centrifuging to obtain enzymes.

The present invention also provides a process for the production of high titer of cellulases and/or hemicellulases enzymes, the method comprises conducting fermentation employing *Penicillium funiculosum* MRJ-16 mutant in a fermentation media comprising, the process comprising
(a) preparing fermentation media using cellulose or acid pretreated lignocellulosic biomass (1-5% w/v) and soya flour or defatted soya flour or de-oiled soya cake (1-5% w/v), followed by inoculation with about 10% active liquid seed of *Penicillium funiculosum* MRJ-16;
(b) subjecting the *Penicillium funiculosum* MRJ-16 culture to fermentation in an aerated fermenter at about 30° C., pH adjusted to 5.5, aeration above 20% for 96 hours; The
(c) collecting the enzyme broth after about 96 hours of fermentation, and centrifuging to obtain the clear enzyme broth.

In accordance with the present invention, the soya flour may be defatted soya flour or plain soya flour. In accordance with the present invention, enzymes produced by *Penicillium funiculosum* MRJ-16 mutant as provided in the present invention are used with mycelia for the saccharification of acid pretreated lignocellulosic biomass. The aeration during the fermentation at all times is maintained above 30%.

In an embodiment of the present invention pre-treated biomass used in accordance with the present invention includes, but is not limited to, rice straw, wheat straw, corn stover, cotton stalk etc. In another embodiment, cellulose and pretreated lignocellulosic biomass can be used together in a mixture.

EXAMPLES

The following examples are set forth below to illustrate the methods and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

Example 1—Production of Enzymes Using Preparatory Media

Fermentation process was carried out in an aerated stirred tank bioreactor of 7 L glass jacketed vessel with 5 L working volume. The media components of fermentation media used were 5 g/L ammonium sulphate, 6 g/L $KH_2PO_4$, 1 g/L $MgSO_4.7H_2O$, 5 g/L $CaCO_3$, 2.5 g/L glycerol, 30 g/L corn steep solids, 30 g/L cellulose and 2 ml/L Tween-80. The fermenter containing 4.5 L medium was sterilized at 120° C. for 20 minutes. After cooling, the temperature was kept at 30° C., pH adjusted to 5.5, aeration above 50% followed by inoculation with 10% active liquid seed of *Penicillium funiculosum* MRJ-16 mutant. The pH during entire fermentation process was not regulated and no nutrients were added; only aeration was maintained above 30%. After 96 hours of fermentation, the enzyme broth was collected, centrifuged and analysis of clear enzyme broth was done. Enzyme activities were analyzed by T. K Ghose method and protein analyzed by BCA method. The results of enzyme analysis obtained were 15 g/L of protein, 65 IU/ml of β-glucosidase and 5.8 filter-paper units (FPU)/ml of filter paper activity.

The analysis of enzyme broth in the present invention may be done according to the known methods, such as methodologies provided in Ghose, T. K., 1987; Measurement of cellulase activities; Pure Appl. Chem. 59, 257-268; or Smith, P. K., Krohn, R. I., Hermanson, G. T., Mallia, A. K., Gartner, F. H., Provenzano, M. D., Fujimoto, E. K., Goeke, N. M., Olson, B. J., and Klenk, D. C. (1985) Measurement of protein using bicinchoninic acid. *Anal. Biochem* 150, 76-85.

Example 2—Production of Enzymes Using Corn Steep Liquid as Nitrogen Source

Cultivation of *P. funiculosum* MRJ-16 mutant was conducted under conditions and media composition identical to example no. 1 except that the corn steep liquor was used as nitrogen source instead of corn steep solids. This was done in order to economize the process and to check whether corn steep quality change will affect the enzyme producing capability of mutant strain. As mentioned above, enzyme broth collected after 96 hours of fermentation assayed and gave 15.4 g/L of protein, 66 IU/ml of β-glucosidase and 6.2 FPU/ml of filter paper activity.

Example 3—Production of Enzymes Using Urea or Sodium Nitrate as Nitrogen Source

The *P. funiculosum* MRJ-16 mutant was cultivated under conditions similar to example no. 2 except that the inorganic nitrogen source i.e. Urea (0.1%) or sodium nitrate (0.5%) was used instead of corn steep liquid. Urea is cheap and easily available nitrogen source. Enzyme broth harvested after 96 hours of fermentation and analyzed which gave 17 g/L of protein, 60 IU/ml of β-glucosidase and 6.7 FPU/ml of filter paper activity in case of urea; 16.5 g/L of protein, 56 IU/ml of β-glucosidase and 6.4 FPU/ml of filter paper activity in case of sodium nitrate.

Example 4—Production of Enzymes Using Pre-Treated Biomass as Carbon Source

Enzyme production from *P. funiculosum* MRJ-16 mutant strain was carried out under the conditions and media composition as described in example no. 2. Acid pretreated lignocellulosic biomass such as sugarcane bagasse/rice straw/wheat straw was used as carbon source, quantity similar to that of cellulose. Pretreatment was done at 0.5-1.5% w/w sulfuric acid concentration, temperature 110-160° C. for 10-30 minutes. After 96 hours of cultivation results obtained were 17.6 g/L of protein, 72 IU/ml of β-glucosidase and 6.5 FPU/ml of filter paper activity.

Example 5—Production of Enzymes Using Pre-Treated Biomass and Cellulose as Carbon Source Cultivation of P. funiculosum MRJ-16 mutant strain was conducted under conditions and media composition identical to example no. 4. Acid pretreated lignocellulosic biomass such as sugarcane bagasse/rice straw/wheat straw along with cellulose in 1:1 or 1:2 ratios was used as carbon source. Analytical determination of enzyme broth gave results, 18 g/L of protein, 78 IU/ml of β-glucosidase and 7.2 FPU/ml of filter paper activity.

Example 6—Production of Enzymes Using Cellulose and Soya Flour

Cultivation of P. funiculosum MRJ-16 mutant strain was conducted under conditions identical to example no. 1. However, no media components mentioned above in example no. 1 were used and only cellulose, defatted soya flour or plain soya flour, both at concentration of 1-5% w/v were added into the water, pH was adjusted to 5-5.5 and autoclaved at 120° C. for 20 minutes. Fermentation was carried out at 30° C. for 96 hours. Analytical determination of enzyme broth harvested gave results, 18 g/L of protein, 73 IU/ml of β-glucosidase and 7.6 FPU/ml of filter paper activity. Thus, media contained only cellulose and soya flour was used for enzyme production.

Example 7—Production of Enzymes Using Pre-Treated Biomass and Soya Flour

Enzyme production using P. funiculosum MRJ-16 mutant was conducted under conditions identical to example no. 6 except cellulose was replaced by acid pretreated lignocellulosic biomass. Biomass, defatted soya flour or plain soya flour, both at concentration of 1-5% w/v were added into the water, pH was adjusted to 5-5.5 and autoclaved at 120° C. for 20 minutes. Fermentation was carried out at 30° C. for 96 hours and enzyme harvested and analyzed. Results were, 16.8 g/L of protein, 71 IU/ml of β-glucosidase and 7.0 FPU/ml of filter paper activity.

Example 8—Hydrolysis of Pre-Treated Lignocellulosic Biomass

The efficiency of enzyme cocktail produced in example no. 6 was determined by its ability to hydrolyze lignocellulosic biomass such as acid pretreated rice straw and produce sugars like glucose. Hydrolysis was performed at high substrate loading of biomass i.e. 20% at pH 4-5, 50 mM citrate buffer, temperature 50° C. at different enzyme loadings from 1-10 FPU/g of dry biomass. Sugars released were determined at regular interval of time by HPLC. Enzyme cocktail worked efficiently and leads to 59% glucan conversion in 48 hours using enzyme concentration at 5 FPU/g of substrate.

| Enzyme loading (FPU/g) of dry biomass | Glucan Conversion (%) | |
| --- | --- | --- |
| | 24 hr | 48 hr |
| 1 FPU | 19.61 | 29.6 |
| 3 FPU | 37.99 | 46.48 |
| 5 FPU | 42.35 | 59.06 |
| 7 FPU | 55.94 | 68.01 |
| 10 FPU | 67.04 | 75.83 |

Example 9—Hydrolysis of Pre-Treated Lignocellulosic Biomass

The efficiency of enzyme cocktail produced in example no. 7 was determined by its ability to hydrolyze lignocellulosic biomass such as acid pretreated rice straw and produce sugars. Hydrolysis was performed at high substrate loading of biomass i.e. 20% at pH 4-5, 50 mM citrate buffer, temperature 50° C. at different enzyme loadings from 1-10 FPU/g of dry biomass. Sugars released were determined at regular interval of time by HPLC. Enzyme cocktail worked efficiently and leads to 60% glucan conversion in 48 hours using enzyme concentration at 5 FPU/g of substrate.

| Enzyme loading (FPU/g) of dry biomass | Glucan Conversion (%) | |
| --- | --- | --- |
| | 24 hr | 48 hr |
| 1 FPU | 16.53 | 26.8 |
| 3 FPU | 36.8 | 45.87 |
| 5 FPU | 43.54 | 60.4 |
| 7 FPU | 57.20 | 67.85 |
| 10 FPU | 66.54 | 75.16 |

The invention claimed is:

1. A process for cellulases enzyme production employing Penicillium funiculosum MRJ-16 mutant, the process comprising conducting fermentation in a minimum fermentation media, wherein the minimum fermentation media consists of:
   (a) about 1-5% w/v of cellulose or acid pretreated lignocellulosic biomass or a combination thereof as a carbon source; and
   (b) about 1-5% w/v soya flour or defatted soya flour or de oiled soya cake as a nitrogen source.

2. A process for cellulases enzyme production, the process comprising:
   (a) providing a minimum fermentation media consisting of a carbon source and a nitrogen source;
   (b) maintaining the temperature of fermentation media in the range of 25 to 34° C.;
   (c) adjusting the pH of the fermentation media to about 5 to 5.5;
   (d) inoculating the fermentation media with about 10% Penicillium funiculosum MRJ-16 and fermenting in an aerated fermenter;
   (e) allowing the fermentation process for about 96 hours,
   (f) collecting the enzyme broth and centrifuging to obtain enzymes.

3. The process as claimed in claim 2, wherein the minimum fermentation media consists of about 1-5% w/v carbon source selected from cellulose or acid pretreated lignocellulosic biomass or a combination thereof, and about 1-5% w/v soya flour or defatted soya flour or de-oiled soya cake as nitrogen source.

4. The process as claimed in claim 2, wherein the carbon source in the minimum fermentation media is cellulose and acid pretreated lignocellulosic biomass in ratios selected from 1:1 or 1:2.

5. A process for producing cellulases and hemicellulases enzymes, the process comprising the steps of:
   a. preparing media components of minimum fermentation media using only 1-5% w/v carbon source selected from cellulose or acid pretreated lignocellulosic biomass and 1-5% w/v soya flour or defatted soya flour or de-oiled soya cake as nitrogen source;
   b. inoculating the media components of step (a) with 10% *Penicillium funiculosum* MRJ-16;
   c. subjecting the *Penicillium funiculosum* MRJ-16 culture of step (b) to fermentation in an aerated fermenter;
   d. collecting the enzyme broth after the fermentation process of step (c) and subjecting the broth to centrifugation to obtain the enzymes.

6. The process as claimed in claim 2, wherein the pH during the fermentation process is unregulated.

7. The process as claimed in claim 1, wherein the lignocellulosic biomass is selected from rice straw, wheat straw, corn stover, cotton stalk or sugarcane bagasse and the soya flour is selected from defatted soya flour or plain soya flour.

8. The process as claimed in claim 5, wherein the pH during the fermentation process is unregulated.

* * * * *